United States Patent
DiPerna et al.

(10) Patent No.: US 10,660,529 B2
(45) Date of Patent: *May 26, 2020

(54) CARDIAC MONITOR WITH PERTURBATION EVALUATION

(71) Applicant: NATIONAL CARDIAC, INC., Escondido, CA (US)

(72) Inventors: Paul M. DiPerna, Escondido, CA (US); Freeman H. Rose, Jr., Del Mar, CA (US)

(73) Assignee: NATIONAL CARDIAC, INC., Escondido, CA (US)

(*) Notice: Subject to any disclaimer, the term of this patent is extended or adjusted under 35 U.S.C. 154(b) by 82 days.

This patent is subject to a terminal disclaimer.

(21) Appl. No.: 15/643,975

(22) Filed: Jul. 7, 2017

(65) Prior Publication Data

US 2019/0008395 A1 Jan. 10, 2019

(51) Int. Cl.
*A61B 5/02* (2006.01)
*A61B 5/0205* (2006.01)
*A61B 5/0245* (2006.01)
*A61B 5/11* (2006.01)
*A61B 5/00* (2006.01)
*A61B 5/0452* (2006.01)

(52) U.S. Cl.
CPC .......... *A61B 5/0205* (2013.01); *A61B 5/0245* (2013.01); *A61B 5/02055* (2013.01); *A61B 5/0452* (2013.01); *A61B 5/1118* (2013.01); *A61B 5/721* (2013.01); *A61B 5/7235* (2013.01); *A61B 5/4806* (2013.01); *A61B 5/4884* (2013.01); *A61B 2562/0204* (2013.01); *A61B 2562/0219* (2013.01)

(58) Field of Classification Search
None
See application file for complete search history.

(56) References Cited

U.S. PATENT DOCUMENTS

| | | | |
|---|---|---|---|
| 3,412,729 | A | 11/1968 | Smith, Jr. |
| 6,569,095 | B2 | 5/2003 | Eggers |
| 6,940,403 | B2 | 9/2005 | Kail, IV |
| 7,907,996 | B2 | 3/2011 | Prystowsky |
| 7,941,207 | B2 | 5/2011 | Korzinov |
| 8,460,189 | B2 | 6/2013 | Libbus |
| 8,744,561 | B2 | 6/2014 | Fahey |
| 8,774,932 | B2 | 7/2014 | Fahey |

(Continued)

OTHER PUBLICATIONS

International Search Report and Written Opinion, dated Aug. 8, 2018, Application No. PCT/US2018/029174.

*Primary Examiner* — Ankit D Tejani
(74) *Attorney, Agent, or Firm* — Nydegger & Associates

(57) ABSTRACT

Systems and methods for monitoring a heart muscle function identify anomalies in the heart muscle function of a patient, relative to a predetermined cardio-profile. Concurrently, they also detect aberrations in the characteristics of perturbations that may have caused the anomaly. In detail, the aberrations are detected relative to a predetermined response matrix for the perturbation, and characteristics of the perturbation are weighted according to their potential influence on the anomaly. The anomalies that are identified from the cardio-profile are then evaluated relative to the corresponding perturbation aberration to determine whether clinical intervention is warranted.

20 Claims, 1 Drawing Sheet

(56) References Cited

U.S. PATENT DOCUMENTS

2004/0059183 A1 3/2004 Jansen
2007/0287880 A1 12/2007 Ovil
2010/0087744 A1 4/2010 Licata
2012/0101476 A1 4/2012 Curtis
2013/0281816 A1 10/2013 Strauss
2017/0071545 A1* 3/2017 Ritscher ............. A61B 5/02405

* cited by examiner

CARDIAC MONITOR WITH PERTURBATION EVALUATION

FIELD OF THE INVENTION

The present invention pertains generally to systems and methods for monitoring the effect that perturbations may have on a heart muscle function. In particular, the present invention identifies anomalies in the heart muscle function relative to a predetermined cardio-profile. It also concurrently detects aberrations in perturbations that may influence these anomalies. For the present invention, characteristics in the aberrations are detected relative to a predetermined response matrix and they are weighted according to their potential influence on the anomaly. The present invention is particularly, but not exclusively, useful for evaluating heart muscle anomalies that are identified from the cardio-profile, and which result from a particular perturbation aberration that is detected from the response matrix, to determine whether clinical intervention is warranted.

BACKGROUND OF THE INVENTION

It is well known that the heart muscle function of a person can be electronically monitored. It is also well known that the heart muscle function can be graphically presented in an electrocardiogram (EKG) which will indicate when there are irregularities (i.e. anomalies) in the heart function. When presented, the EKG can then be evaluated by clinical personnel to diagnose issues that may be detected, and to determine whether an appropriate clinical intervention is necessary.

Along with other scientific advances, electronic technologies have advanced to the point where continuous monitoring of a heart muscle function is feasible. In particular, it is now possible to monitor a patient's heart muscle function on a continuous, 24 hours-a-day, basis. With this extended monitoring capability, however, it has also become necessary to more accurately detect and ignore the false-positive reactions that would otherwise indicate that a clinical intervention is warranted. Stated differently, not all circumstances that may seem to adversely influence an EKG require an active response.

With the above in mind, the requirement for properly detecting a true positive which requires an active response is essentially two-fold. Firstly, there is the need to accurately identify an anomaly in the heart muscle function, when it occurs. Secondly, it is necessary to evaluate the cause of the anomaly in order to determine whether it is likely to adversely affect the patient's heart muscle function. As indicated above, a false-positive will indicate a need for clinical intervention when none is actually needed. On the other hand, a true positive may require immediate intervention.

As opposed to a chronic condition that develops over time, and which can be more thoroughly evaluated, an intermediate or short-term incident or accident may not tolerate such a delay. Typically, short-term incidents result from an egregious happenstance in a patient's normal activity that has a pronounced influence on the patient and his/her heart function. Like the heart muscle function itself, a perturbation that causes an anomaly in the heart muscle can be electronically monitored. Moreover, a heart muscle function anomaly and a causal perturbation can be monitored concurrently, and then simultaneously evaluated.

In light of the above, it is an object of the present invention to provide systems and methods for monitoring a heart muscle function that concurrently monitors for anomalies in a heart muscle function and for aberrations in a perturbation that causes the anomaly, for an evaluation of their interaction with each other to determine whether clinical intervention is warranted. Another object of the present invention is to provide systems and methods for monitoring a heart muscle function that identify anomalies relative to a predetermined cardio-profile and detect aberrations relative to a weighted response matrix, and then simultaneously evaluate the anomalies and aberrations together to determine whether clinical intervention is warranted.

SUMMARY OF THE INVENTION

In accordance with the present invention a computer-based system evaluates anomalies of the heart muscle function of a patient that may be caused, or aggravated, by external influences (i.e. perturbations). For this purpose, the computer includes a cardio-profile that is used for identifying anomalies in the heart muscle function. The computer also includes a response matrix for detecting aberrations (perturbations) due to external influences that are experienced by the patient. Additionally, an evaluator is connected with the cardio-profile and with the response matrix. With these connections, the effects that aberrations detected by the response matrix have on the anomalies that are identified by the cardio-profile can be evaluated.

For a set-up of a system for the present invention, a cardiac sensor is positioned with the patient and is connected with the computer. With this connection, cardiac input data is collected in real time by the cardiac sensor for use by the computer in identifying anomalies in the heart muscle function. The system also includes at least one perturbation sensor which is positioned with the patient and connected with the computer. With this connection, perturbation input data is collected from the patient in real time, simultaneously with the cardiac input data, for use by the computer to detect aberrations that affect the heart muscle function.

The cardiac sensor that is to be used for the present invention is preferably an electrocardiogram (EKG) of a type well-known in the pertinent art. Accordingly, the cardio-profile is structured to include measurable parameters that will correspond with the cardiac input data. Further, the cardio-profile is pre-configured to establish acceptable ranges for variations in individual parameters of the cardiac input data. As envisioned for the present invention, the cardio-profile is preferably established by a physician for a particular patient (i.e. it can be patient-specific). On the other hand, the present invention also envisions that the cardio-profile can be prepared and preprogrammed into a computer.

Typical parameters from the heart muscle function are used to structure the cardio-profile. In general, these parameters are based on a waveform of the heart muscle that are created by the cardiac sensor (EKG). For the present invention these parameters will typically be waveform shape characteristics, amplitudes within the waveform, the repetition rate of heart function cycles in the waveform, variability of the waveform shape, discontinuities in the waveform, and/or a variability in the repetition rate. As intended for the present invention, an anomaly is identified whenever an individual parameter in the cardiac input data extends beyond an acceptable range in the cardio-profile.

At least one perturbation sensor is provided to collect perturbations that may cause or aggravate an anomaly. The perturbation sensor(s) is(are) positioned with the patient, and is(are) connected to the computer to provide perturbation input data for use by the computer. As noted above, this perturbation input data will be referenced to the response matrix. As intended for the present invention, the anomalies identified with reference to the cardio-profile are then evaluated relative to the aberrations that have been simultaneously detected by the response matrix. This evaluation is done concurrently to determine whether a clinical intervention for the patient is warranted.

For the above-stated purpose, the response matrix includes a plurality of measurable parameters that are typical for the perturbation input data. Each of these parameters will have a dimensional characteristic, and each will have a temporal characteristic. Depending on its expected effect on an anomaly, each characteristic of each measurable parameter is given a respective weighting factor. All of the weighted characteristics are then collectively combined to create the response matrix. Consequently, in an operation of the present invention, each perturbation will generate a uniquely specified aberration which is then used by the computer to evaluate the anomaly that has been identified with reference to the cardio-profile response. Like the cardio-profile disclosed above, the response matrix is preferably established by a physician and is designed specifically for a particular patient. Also, like the cardio-profile the response matrix can be preprogrammed into the computer.

Exemplary characteristics of measurable parameters for inclusion in the response matrix include a magnitude, a duration, a trend, and a rate of change, together with variations and combinations thereof. Further, perturbation sensors will typically be either an accelerometer, a thermometer, an audiometer and/or a potentiometer. Using these sensors, the perturbation input data will typically include environmental data such as local weather conditions, electromagnetic radiation, radioactivity, time of day, climatic considerations, and altitude. The perturbation input data can also include physical data such as stress, trauma, disease, extrinsic exercise/activity level, sleep patterns, and body contacts.

In accordance with the present invention, a methodology for monitoring the heart muscle function of a patient requires creating a cardio-profile and a response matrix as disclosed above, together with an alert for readiness of the system, i.e. battery charge, calibration, and system self-tests. Cardiac input data and perturbation input data can then be collected simultaneously from respective sensors. During a computer operation, anomalies in the heart muscle function of the patient are identified relative to the predetermined cardio-profile. Also, perturbations experienced by the patient are then concurrently detected relative to the predetermined response matrix. The effect the perturbations have on the anomalies are evaluated to determine whether a clinical intervention for the patient is warranted.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
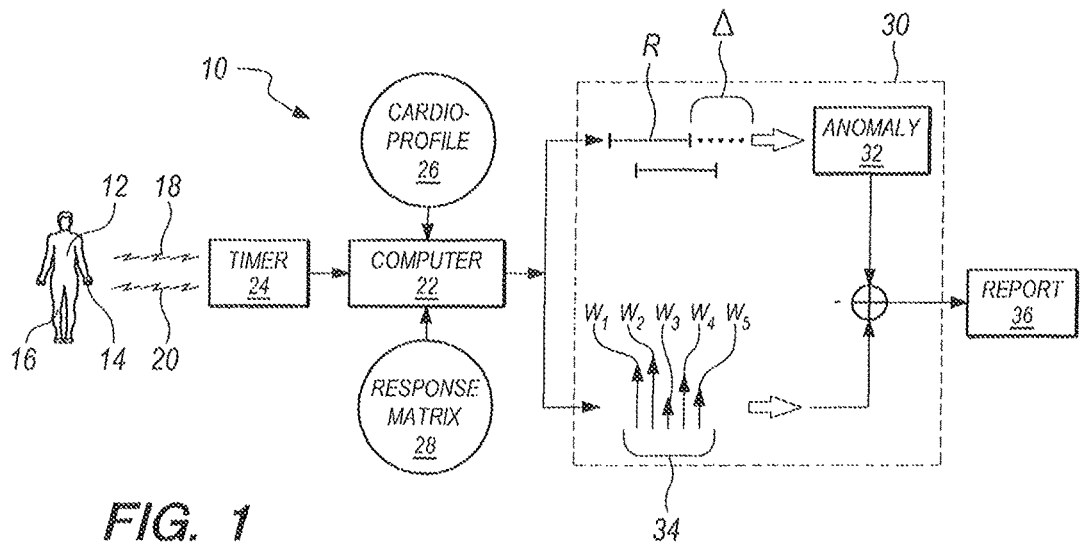
FIG. 1 is a combined schematic presentation of system components and data manipulations required for the present invention.

Referring initially to FIG. 1, a system for monitoring a heart muscle function in accordance with the present invention is shown, and is generally designated 10. As shown, the system 10 includes a cardiac sensor 12 and at least one perturbation sensor 14. Both of the sensors 12 and 14 are appropriately positioned with a patient 16. As envisioned for the present invention, the cardiac sensor 12 will be an electrocardiogram (EKG) of a type well-known in the pertinent art. On the other hand, the perturbation sensor(s) 14 will typically be selected from a group that includes an accelerometer, a thermometer, an audiometer and/or a potentiometer. In use, the cardiac sensor 12 is intended to transmit cardiac input data 18, and the perturbation sensor 14 is intended to transmit perturbation input data 20 to a computer 22. For the present invention, the computer 22 may be either positioned together with the sensors 12 and 14 directly on the patient 16, or it can be located at a remote site.

As envisioned for the system 10, the cardiac input data 18 will include measurable parameters taken from an EKG that will typically include waveform shape characteristics, amplitudes within the waveform, the repetition rate of heart function cycles in the waveform, variability of the waveform shape, discontinuities in the waveform, and/or a variability in the repetition rate. On the other hand, the perturbation input data 20 will typically include environmental data such as local weather conditions, electromagnetic radiation, radioactivity, time of day, climatic considerations, and altitude. Moreover, together with the environmental data, the perturbation input data 20 may also include physical data pertaining to the patient 16 such as stress, trauma, disease, extrinsic exercise/activity level, sleep patterns, and body contacts, together with an alert for readiness of the system, i.e. battery charge, calibration, and system self-tests. As shown in FIG. 1, a timer 24 is provided with the computer 22 to accurately annotate the simultaneous occurrence of cardiac input data 18 and perturbation input data 20.

FIG. 1 also shows that the computer 22 incorporates a cardio-profile 26 and a response matrix 28. Further, the computer 22 functions together with an evaluator 30. In particular, the evaluator 30 is provided to evaluate the results that are obtained by an operation of the cardio-profile 26 on the cardiac input data 18. Also, the evaluator 30 is provided to evaluate an operation of the response matrix 28 on the perturbation input data 20.

For the present invention, the cardio-profile 26 is structured to include measurable parameters that will correspond with the cardiac input data 18. Further, the cardio-profile 26 is pre-configured to establish acceptable ranges R for variations in individual parameters of the cardiac input data 18. In particular, the cardio-profile 26 will identify an anomaly 32 in a heart muscle function of the patient 16 whenever a variation results as a deviation Δ that extends beyond the range R.

The response matrix 28 for the system 10 includes a plurality of measurable parameters that will correspond with the perturbation input data 20. In particular, these parameters will be typical for respectively different types of perturbations, and each perturbation will have unique dimensional characteristics and unique temporal characteristics. For purposes of the present invention, the parameters in each perturbation are given a weighting factor according to its potential influence on a particular type of anomaly. All of the weighted characteristics are then collectively combined to create the response matrix 28. Accordingly, when a perturbation is detected in the perturbation input data 20, pertinent weighted parameters are selected from the response matrix 28 to create a specified aberration 34.

As indicated in FIG. 1, whenever an anomaly 32 is identified simultaneously with the detection of a specified aberration 34, the anomaly 32 is concurrently compared relative to the specified aberration 34 by the evaluator 30. Based on this comparison by the evaluator 30, a determination is made regarding the severity and significance of the anomaly 32. Specifically, this determination will be presented in a report 36 that indicates whether clinical intervention is warranted.

Figure 2:
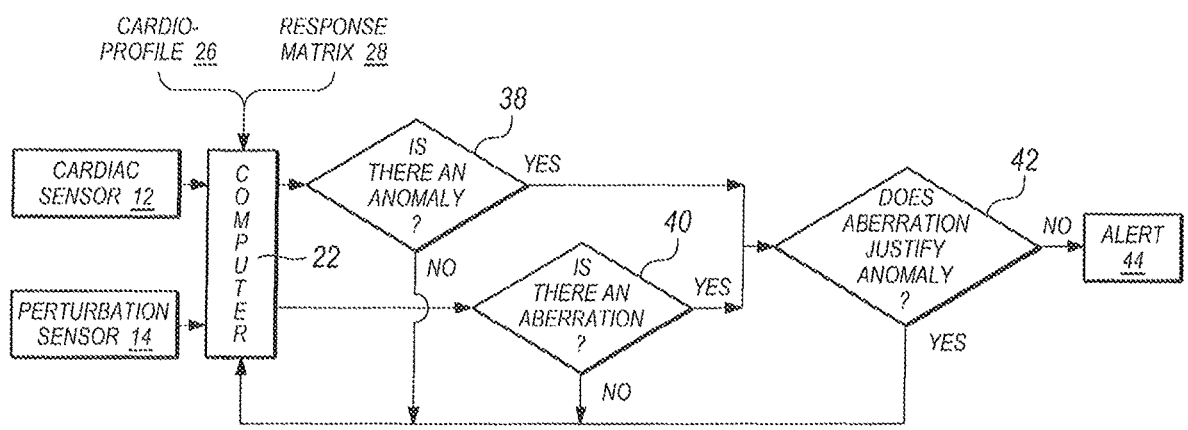
FIG. 2 is a logic flow chart of the interactive tasks required for an operation of the present invention.

In FIG. 2, the inquiry block 38 indicates that the system 10 determines whether an anomaly 32 has occurred in the heart muscle function of the patient 16. Inquiry block 40 indicates that the system 10 also determines whether a specified aberration 34 has been simultaneously detected. Further, inquiry block 42 indicates that when an anomaly 32 has been identified and a specified aberration 34 has been detected, a determination is made as to whether the specified aberration 34 justifies the anomaly 32. In the event the anomaly 32 is not justified, an alert 44 indicates that a report 36 has been given. It will be noted that, as a safety factor, FIG. 2 indicates an alert 44 will be given when an anomaly 32 is identified, even though no specified aberration 34 has occurred. Stated differently, no report 36 is given when the anomaly 32 is justified.

While the particular Cardiac Monitor with Perturbation Evaluation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for monitoring the heart muscle function of a patient which comprises:
   a computer including a cardio-profile for identifying anomalies in the heart muscle function, and a weighted response matrix for detecting specified aberrations in a reaction of the patient to influences experienced by the patient, wherein the specified aberrations are created in the weighted response matrix with weighting factors based on a potential influence of the specified aberration on a particular type of anomaly caused during short-term incidents/accidents resulting in patient stress/trauma;
   a cardiac sensor connected to the computer to provide cardiac input data including a plurality of measurable parameters having quantifiable characteristics, for use by the cardio-profile in the computer to identify anomalies in accordance with the cardio-profile;
   at least one perturbation sensor connected to the computer to provide perturbation input data including a plurality of measurable parameters having quantifiable characteristics, for use by the weighted response matrix in the computer to detect aberrations in accordance with the weighted response matrix; and
   an evaluator connected with the computer for evaluating the anomalies identified from the cardio-profile relative to specified aberrations detected by the weighted response matrix, wherein the evaluation determines whether an otherwise reportable anomaly does not justify a clinical intervention for the patient.

2. The system recited in claim 1 wherein the weighted response matrix comprises:
   a plurality of measurable parameters taken from the perturbation input data, wherein each measurable parameter results from an influence on the patient and has a dimensional characteristic and a temporal characteristic; and
   a plurality of weighting factors, wherein each characteristic of each measurable parameter is given a respective weighting factor, and wherein weighted characteristics are selectively combined to collectively create the specified aberration for use by the computer in determining whether a clinical intervention for the patient is justified.

3. The system recited in claim 2 wherein quantifiable characteristics of a measurable parameter in the perturbation input data are selected from the group consisting of: a magnitude, a duration, a trend, and a rate of change, together with variations and combinations thereof.

4. The system recited in claim 1 wherein the cardiac sensor is an electrocardiogram (EKG), and each perturbation sensor is selected from the group consisting of accelerometers, thermometers, audiometers and potentiometers.

5. The system recited in claim 1 wherein the perturbation input data includes environmental data resulting from local weather conditions, electromagnetic radiation, radioactivity, time of day, climatic considerations, and altitude; together with physical data resulting from stress, trauma, disease, extrinsic exercise/activity level, sleep patterns, and body contacts and an alert for readiness of the system, i.e. battery charge, calibration, and system self-tests.

6. The system recited in claim 1 wherein the cardio-profile establishes acceptable ranges for variations in individual parameters of the cardiac input data.

7. The system recited in claim 6 wherein quantifiable characteristics of the measurable parameters from the cardiac input data are based on a waveform of the heart muscle and are selected from the group consisting of waveform shape characteristics, amplitudes within the waveform, the repetition rate of heart function cycles in the waveform, variability of the waveform shape, discontinuities in the waveform, and variability of the repetition rate.

8. The system recited in claim 7 wherein an anomaly is identified when an individual parameter in the cardiac input data extends beyond an acceptable range in the cardio-profile.

9. The system recited in claim 1 further comprising a timer incorporated with the computer for establishing a concurrent time frame for simultaneously evaluating anomalies and aberrations.

10. A method for using a computer to monitor the heart muscle function of a patient which comprises the steps of:
    collecting cardiac input data, including measurable parameters having quantifiable characteristics, from a cardiac sensor positioned with the patient for use in a cardio-profile;
    identifying anomalies in the heart muscle function of the patient relative to the cardio-profile;
    collecting perturbation input data, including measurable parameters with quantifiable characteristics, from at least one perturbation sensor positioned with the patient for use in a weighted response matrix;
    detecting aberrations in a reaction of the patient to perturbation influences experienced by the patient;
    creating specified aberrations for the weighted response matrix with weighting factors based on a potential influence of the specified aberration on a particular type of anomaly caused during short-term incidents/accidents resulting in patient stress/trauma;

simultaneously evaluating the anomalies identified from the cardio-profile in the identifying step with the specified aberrations created for the weighted response matrix in the creating step, wherein the evaluation determines whether an otherwise reportable anomaly does not justify a clinical intervention for the patient.

11. The method recited in claim 10 wherein the cardio-profile used in the identifying step is created by following the steps of:
selecting a plurality of measurable parameters from the cardiac input data; and
establishing acceptable ranges for variations in individual parameters of the cardiac input data.

12. The method recited in claim 11 wherein the cardiac sensor is an electrocardiogram (EKG), and aberrations are detected by a perturbation sensor selected from the group consisting of accelerometers, thermometers, audiometers and potentiometers.

13. The method recited in claim 11 wherein quantifiable characteristics of the measurable parameters from the cardiac input data are based on a waveform of the heart muscle and are selected from the group consisting of waveform shape characteristics, amplitudes within the waveform, the repetition rate of heart function cycles in the waveform, variability of the waveform shape, discontinuities in the waveform, and variability of the repetition rate.

14. The method recited in claim 13 wherein an anomaly is identified when an individual parameter in the cardiac input data extends beyond an acceptable range in the cardio-profile.

15. The method recited in claim 10 wherein the detecting step includes the steps of:
selecting a plurality of measurable parameters taken from the perturbation input data, wherein each measurable parameter results from an influence on the patient and has a dimensional characteristic and a temporal characteristic;
giving each characteristic of each measurable parameter a respective weighting factor according to the influence the characteristic may have on the anomaly; and
combining the weighted characteristics to collectively create the specified aberration for use in determining whether a clinical intervention for the patient is justified.

16. The method recited in claim 15 wherein quantifiable characteristics of a measurable parameter are selected from the group consisting of a magnitude, a duration, a trend, and a rate of change, together with variations and combinations thereof.

17. The method recited in claim 16 wherein the perturbation input data includes environmental data resulting from local weather conditions, electromagnetic radiation, radioactivity, time of day, climatic considerations, and altitude, together with physical data resulting from stress, trauma, disease, extrinsic exercise/activity level, sleep patterns, and body contacts and an alert for readiness of the system, i.e. battery charge, calibration, and system self-tests.

18. The method recited in claim 10 further comprising the step of establishing a concurrent time frame for simultaneously evaluating anomalies and aberrations.

19. A method for using a computer to monitor the heart muscle function of a patient which comprises the steps of:
collecting cardiac input data from a cardiac sensor positioned with the patient;
selecting a plurality of measurable parameters having quantifiable characteristics from the cardiac input data;
establishing acceptable ranges for variations in individual parameters of the cardiac input data to create a predetermined cardio-profile for the patient;
collecting perturbation input data from at least one perturbation sensor positioned with the patient;
selecting a plurality of measurable parameters having quantifiable characteristics taken from the perturbation input data, wherein each measurable parameter results from an influence on the patient and has a dimensional characteristic and a temporal characteristic;
giving each characteristic of each measurable parameter in the perturbation input data a respective weighting factor according to the influence the characteristic may have on the cardiac input data;
combining the weighted characteristics to collectively create a predetermined weighted response matrix of specified aberrations;
creating specified aberrations for a weighted response matrix with weighting factors based on a potential influence of the specified aberration on a particular type of anomaly caused during short-term incidents/accidents resulting in patient stress/trauma;
identifying anomalies in the heart muscle function of the patient relative to the predetermined cardio-profile;
detecting specified aberrations in a reaction of the patient to perturbation influences experienced by the patient, wherein the specified aberrations are detected relative to the predetermined weighted response matrix; and
evaluating the anomalies identified from the cardio-profile in the identifying step with the specified aberrations detected by the weighted response matrix in the detecting step, wherein the evaluation determines whether an otherwise reportable anomaly does not justify a clinical intervention for the patient.

20. The method recited in claim 19 wherein the cardiac sensor is an electrocardiogram (EKG), and each perturbation sensor is selected from the group consisting of accelerometers, thermometers, audiometers and potentiometers.

* * * * *